United States Patent [19]
Mihcakan et al.

[11] Patent Number: 5,505,074
[45] Date of Patent: Apr. 9, 1996

[54] APPARATUS AND METHOD FOR DETERMINING MINIMUM MISCIBILITY PRESSURE

[75] Inventors: I. Metin Mihcakan, Istanbul, Turkey; Fred H. Poettmann; Richard L. Christiansen, both of Littleton, Colo.

[73] Assignee: Marathon Oil Company, Findlay, Ohio

[21] Appl. No.: 271,927

[22] Filed: Jul. 7, 1994

[51] Int. Cl.$^6$ ............................. G01N 7/00; G01N 33/26
[52] U.S. Cl. ..................... 73/64.45; 73/54.15; 73/61.78; 73/19.01
[58] Field of Search .............................. 73/64.45, 54.15, 73/64.51, 61.78, 19.01, 61.77

[56] References Cited

U.S. PATENT DOCUMENTS

| | | | |
|---|---|---|---|
| 2,654,243 | 10/1953 | Colthup et al. | 73/53 |
| 3,854,324 | 12/1974 | Altshuler et al. | 73/64.1 |
| 4,276,383 | 6/1981 | Leighton et al. | 435/291 |
| 4,329,869 | 5/1982 | Toda | 73/19 |
| 4,330,385 | 5/1982 | Arthur et al. | 204/195 R |
| 4,455,860 | 6/1984 | Cullick et al. | 73/19 |
| 4,627,273 | 12/1986 | Christiansen et al. | 73/61.1 |
| 4,862,729 | 9/1989 | Toda et al. | 73/19 |

OTHER PUBLICATIONS

R. L. Christiansen et al., "Rapid Measurement of Minimum Miscibility Pressure Using the Rising Bubble Apparatus," SPE 13114, Sep. 1984.
R. L. Christiansen et al., "Rapid Measurement of Minimum Miscibility Pressure With the Rising-Bubble Apparatus," SPE Reservoir Engineering, Nov. 1987, pp. 523–527.
R. A. Harmon et al., "Vapor Density Measurement for Estimating Minimum Miscibility Pressure," SPE 15403, Oct. 1986.

*Primary Examiner*—Hezron E. Williams
*Assistant Examiner*—J. David Wiggins
*Attorney, Agent, or Firm*—Jack L. Hummel; Jack E. Ebel

[57] ABSTRACT

An apparatus and method for determining the minimum miscibility pressure of a system comprising a gas and a liquid. A liquid-filled tube is equilibrated at a predetermined temperature and initial pressure, and pressure changes are determined as a single gas bubble is launched, rises through the tube, and stabilizes in the liquid. The measurements are repeated with fresh liquid at a series of different predetermined pressures. The minimum miscibility pressure is obtained either by finding the final pressure at which the time between launch and stabilization is constant or by evaluating the derivative of an empirically derived relationship between initial pressure and final pressure.

24 Claims, 7 Drawing Sheets

FIG. 7

APPARATUS AND METHOD FOR DETERMINING MINIMUM MISCIBILITY PRESSURE

BACKGROUND OF THE INVENTION

1. Field of Invention

This invention relates generally to an apparatus and method for determining the minimum miscibility pressure (MMP) for a gas in a liquid, and in particular, to an apparatus and method for determining the minimum miscibility pressure for a gas in a liquid based on pressure changes in a rising bubble apparatus.

2. Description of Related Art

An enhanced oil recovery process is a process for increasing the production of oil from a subterranean formation by injecting a liquid or a gas into the formation in a quantity sufficient to flood the formation. When designing a gas flood, it is important to determine the minimum pressure at which the flood gas is miscible in the reservoir oil. Conducting a gas flood at or slightly above the MMP increases oil production because the capillary forces are eliminated and the oil is displaced as a single phase. Also, when the gas is dissolved in the oil, the oil volume increases and the viscosity decreases. If the formation-pressure is less than the MMP, the pressure must be increased before miscible oil displacement can occur. However, increasing the pressure of a gas injected into a subterranean formation pressure substantially above the MMP increases operating costs, increases the risks of undesirable formation fracturing, and creates additional hazards for personnel, without significantly improving oil production. Thus, it is desirable to perform laboratory experiments to determine the MMP of the desired flooding gas in the oil at the temperature of the formation.

One method for determining the MMP of a system comprising a gas and a liquid is to observe the behavior of gas bubbles rising through the liquid. U.S. Pat. No. 4,627,273 to Richard L. Christiansen and Hiemi Kim describes an apparatus and method for determining the minimum miscibility pressure (MMP), the pressure at which a gas and a liquid are miscible. A single gas bubble is injected into a non-horizontal, transparent glass tube containing the liquid at a fixed temperature and a predetermined pressure. The behavior of the bubble is observed as it rises through the liquid. Additional observations are made at a series of pressures from low to high, to determine the lowest pressure at which a bubble exhibits characteristic multiple contact miscibility behavior.

Initially, the gas bubble is nearly spherical. If the pressure is below the MMP, the top of the bubble remains spherical, and the bottom interface of the bubble becomes flat. The gas bubble retains its nearly spherical shape as it rises, and the size of the bubble decreases as material is transferred from the bubble to the surrounding liquid. As the pressure is increased to approach the MMP the flatness of the bottom interface of the bubble vanishes, and the tail-like features develop along the sides and/or the bottom of the bubble. When the pressure is slightly below the MMP, the contents of the bubble quickly disperse in the liquid, and the bottom interface of the bubble severely deteriorates. If the pressure is at or slightly above the MMP, the gas is multiple contact miscible in the liquid, and the full miscibility is achieved in stages. The bubble can not retain its integrity and breaks up into two or more smaller bubbles, which eventually dissipate, upon rise in the liquid.

However, the method of Christiansen and Kim is sometimes difficult to apply because the bubbles may rise too rapidly for easy observation. Further, observations are subjective, and the quality of the results depends upon the skill of the operator. If the apparatus is to be used with opaque liquids, it can be difficult to construct. For example, the tube must be flattened to facilitate visibility of the bubble, and the bubble injection mechanism must be centered to prevent growing bubbles from contacting the walls of the tube prior to launch. The need to use a transparent glass tube also limits the maximum temperature and pressure at which measurements can be made. In addition, it is desirable to make more accurate MMP determinations.

Accordingly, an object of the present invention is to provide an apparatus and method which allow more objective MMP determinations that are less dependent than current methods upon the operator's skill.

A further object of the present invention is to provide an apparatus which is simpler to construct and which allows measurements at high temperatures and pressures.

Yet another object of the present invention is to provide an apparatus and method with which more accurate results can be obtained.

SUMMARY OF THE INVENTION

To achieve the foregoing and other objects, and in accordance with the purposes of the present invention, as embodied and broadly described herein, one characterization of the present invention comprises a rising bubble apparatus for determining the MMP of a system comprising a gas and a liquid. The apparatus comprises a tube having an open end and a closed end. The tube is positioned within a substantially enclosed pressure vessel so that the closed end is higher than the open end. The apparatus also comprises means for forming bubbles at the bottom of the tube and launching the bubbles into the tube. The tube has an open bottom and a closed top and is capable of being filled with a liquid. In addition, the apparatus comprises means for measuring liquid pressure changes occurring in the tube while bubbles of gas form in the tube and move through the liquid.

Another characterization of the present invention comprises a method for determining the MMP of a gas/liquid combination. A non-horizontal tube is filled with the liquid, and the liquid is allowed to equilibrate at a predetermined temperature and initial pressure. A single gas bubble is formed and launched at the bottom of the liquid-filled tube. The elapsed time and pressure changes in the liquid are measured simultaneously while the bubble forms and rises through the liquid in the tube. A bubble launch time, signifying the time when the bubble begins to rise through the liquid column, is the time at which the liquid pressure reaches a maximum value. A final time, signifying the time when the bubble reaches equilibrium with the liquid, is the time when the liquid pressure becomes constant at a final pressure. The tube is then emptied. The measurement process is repeated at least one time, with the liquid at a different predetermined initial pressure for each repetition, until a range of final pressures is determined, within which range the difference between the final time and the launch time is substantially constant. The highest final pressure within the range is the MMP of the gas/liquid combination at the predetermined temperature.

Yet another embodiment comprises a method for determining the MMP of a system comprising a gas and a liquid.

A non-horizontal tube is filled with a liquid, and the liquid is allowed to equilibrate at a predetermined temperature and initial pressure. A single gas bubble is formed and launched into the liquid-filled tube. The elapsed time and pressure changes in the liquid are measured simultaneously while the bubble forms and rises through the liquid in the tube. A final pressure is determined when the bubble reaches equilibrium with the liquid. The liquid in the tube is replaced. The process is repeated at least one time, with the liquid at a different predetermined initial pressure for each repetition. An empirical mathematical function is derived, relating the initial pressure to the final pressure. The derivative of the function with respect to initial pressure is also determined. The final pressure at which the derivative of the mathematical relationship is zero is the MMP for a vaporization process. For a condensation process, the MMP is the final pressure at which the derivative is undefined.

BRIEF DESCRIPTION OF THE DRAWINGS

These and other features, aspects, and advantages of the present invention will become better understood with reference to the following description, appended claims, and accompanying drawings where:

DESCRIPTION OF THE PREFERRED EMBODIMENTS

The present invention comprises a method ,and apparatus for determining the minimum miscibility combination of a gas/liquid system. In the following discussion, the term "minimum miscibility pressure" is defined as the pressure at which the interfacial tension at the interface between a gas bubble and a liquid approaches zero as a consequence of a multiple contact process, causing the gas bubble to dissipate. The term "minimum miscibility pressure" is abbreviated throughout this description as "MMP". As utilized throughout this description, the term "gas" refers to any gas which is at least partly miscible in a selected liquid within a predetermined range of temperature and pressure. The gas becomes completely miscible with the liquid via an in situ multiple contact miscibility process. When a liquid and a gas are multiple contact miscible material is exchanged between the liquid and the gas, thereby forming a liquid and a gas having different compositions. Additional material is exchanged until liquid and gas compositions are reached that are fully miscible. In a vaporization process, material is transferred from the liquid to the gas, and in a condensation process, material is tranferred from the gas to the liquid. The present apparatus and method simulate multiple contact miscibility processes.

One application of determining the MMP of a gas in a liquid is to determine the optimum pressure for a gas flood in an enhanced oil recovery operation. Thus, the liquid used in the present invention may be a hydrocarbon, such as a crude oil. The gases with the greatest commercial potential for enhanced oil recovery operations include $CO_2$, $N_2$, $H_2S$, and alkanes having up to five carbon atoms. These gases may be partly miscible when they are initially injected at practical operating pressures into a subterranean formation bearing crude oil.

Figure 1:
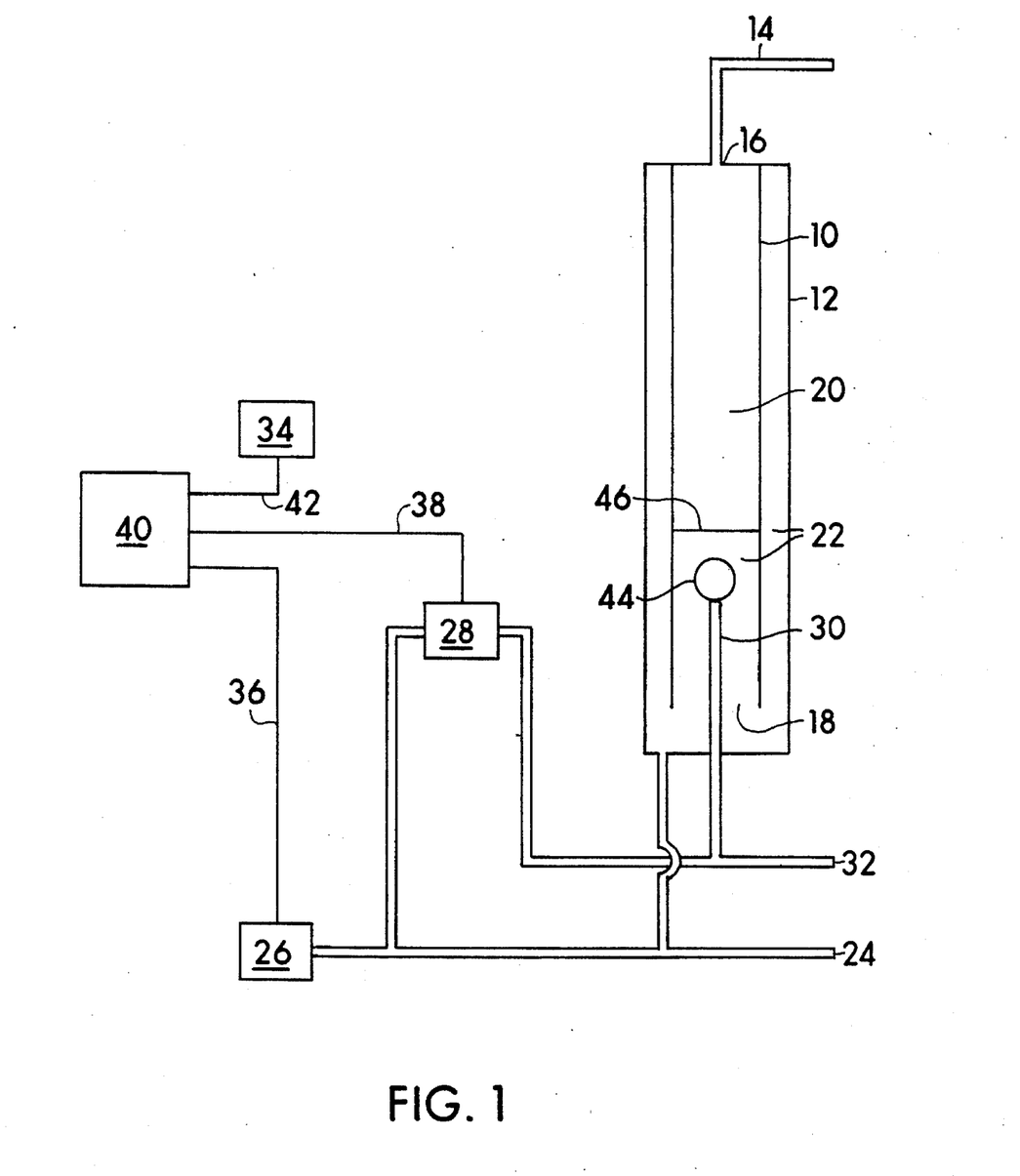
FIG. 1 is a schematic diagram of one embodiment of the rising bubble apparatus of the present invention.

The rising bubble apparatus shown schematically in FIG. 1 comprises a tube 10 mounted in a pressure vessel 12. A first liquid line 14 enters the top of tube 10 and connects the tube with a first liquid reservoir, not shown. The top 16 of the tube 10 is otherwise closed. The bottom 18 of tube 10 is open, and the tube is positioned at an angle from horizontal. The upper portion of the tube contains a first liquid 20, and the lower portion of the tube and the pressure vessel contain a second liquid 22. A second liquid line 24, provides fluid communication between a reservoir of the second liquid, not shown, the interior of the pressure vessel 12, an absolute pressure measuring device 26, and a differential pressure measuring device 28. A means for introducing bubbles of gas 30 is at or near the bottom of tube 10. As shown, means 30 is a hollow needle centered on the longitudinal axis of the tube, A gas line 32 provides fluid communication between a source of gas, not shown, the means for introducing gas bubbles 30, and differential pressure measuring device 28. A means 34 is also provided for measuring time while the bubbles are in the tube 10.

As is apparent to one skilled in the art, the tube need not be transparent and thus can be constructed of a material capable of withstanding higher temperatures and pressures than the glass windowed pressure vessels required in prior art rising bubble apparatuses. The pressure measuring devices 26 and 28 can be an absolute pressure transducer and a differential pressure transducer, respectively. Differential pressure measuring device 28 may be used to increase the precision of the absolute pressure determination obtained with the absolute pressure measuring device 26. If the absolute pressure determination is sufficiently precise, the differential pressure determination may be unnecessary. As illustrated in FIG. 1, the electrical signals created by the absolute and differential pressure, transducers can be transmitted via transmission means 36 and 38, respectively, to a storage and output device 40. As is apparent to one skilled in the, art, the storage device can be a computer equipped with software for receiving, storing, and retrieving data.

The apparatus shown in FIG. 1 may be used to determine MMP values. The pressure vessel 12 and the tube 10 are charged with second liquid 22. Then tube 10 is filled with the, first liquid 20, while displacing the excessive amount of the second liquid 22, selected to be immiscible with the first liquid 20, out of the pressure vessel 12. For example, in a simulation of a gas flood for an enhanced oil recovery process, the first liquid is a crude oil. The second liquid is water, which is immiscible with the crude oil. The contents of the pressure vessel and the tube are allowed to equilibrate at a predetermined temperature and pressure. The temperature and pressure of the contents of pressure vessel 12 and tube 10 and are controlled by temperature and pressure control means, not shown. A gas bubble 44 is then introduced from line 32 at the bottom of the tube 10 via means 30. If simulating a gas flood process, the gas could be $CO_2$, $N_2$, $H_2S$, a hydrocarbon comprising at least one alkane having up to 5 carbon atoms, or a mixture thereof. When the interfacial tension of the gas/second liquid interface decreases to a value approximately equal to the buoyant force of the gas in the bubble 44, the bubble is launched and begins to rise through the second liquid 22 at the bottom of tube 10 until it reaches the interface 46 between the first and second liquids 20 and 22. The multiple content miscibility process begins between the bubble and the first liquid 20. As a result, the interface tension between the intermediate composition gas and the liquid decreases. When the interface tension becomes less than the buoyant force of the bubble, the bubble breaks through interface 46 and rises in tube 10 through the first liquid 20 in tube 10. The multiple contact miscibility process continues to take place as the bubble rises. Pressure measurements are made with at least one of pressure measuring devices 26 and 28 and times are determined by means 34 as the bubble forms, is launched, and rises. The pressures are transmitted via electrical lines 36 and/or 38 and stored in storage and output device 40. Times are transmitted via time transmission line 42 and also stored in storage and output device 40. The first liquid in the tube is replaced with fresh liquid which has not been contacted by the gas, and the system is again allowed to equilibrate at a different preselected pressure at the same temperature. A new bubble is allowed to form, launch, and rise, and the pressures and times are measured and stored as described above. The process is repeated at least one time with a different initial pressure.

The measurements may be repeated one or more times without replacing the first liquid in the tube. However, if the gas is miscible in the first liquid, and the liquid composition changes with the introduction of each bubble. Particularly when the vaporization process is the mechanism of miscibility and the initial pressure is near the MMP, repeating measurements without changing the first liquid introduces inaccuracies into the MMP determination.

Figure 2:
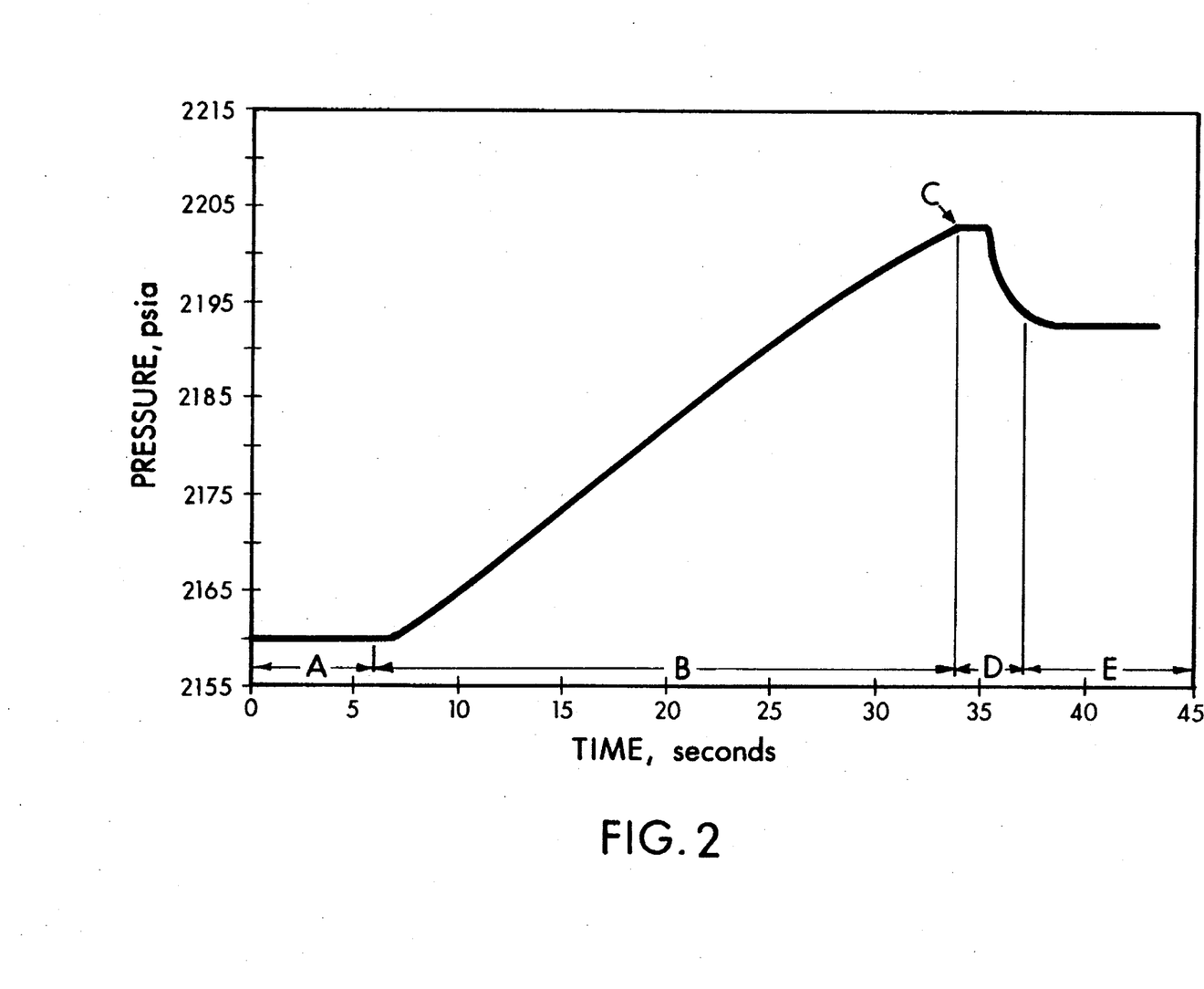
FIG. 2 is a graph of pressure versus time during bubble formation, launch, and rise.

FIG. 2 is a graph showing the changes in pressure during bubble formation, launch, and rising in the apparatus of FIG. 1. The initial pressure of the apparatus was 2160 psia. As indicated by the portion of the graph marked A, the pressure in tube 10 remained constant for about seven seconds, showing that the pressure was initially stable. In section B of the graph, the pressure increased while the bubble formed, reaching a maximum of 2203.5 psia at the launch. The bubble launch is indicated at C. Section D of the graph corresponds to the bubble's rise through the liquid; the pressure decreased to a final pressure of 2193 psia. The time during which bubble rises is designated $t_s$ in the following discussion. Upon completion of the multiple contact miscibility process, the pressure stabilized at the final pressure of 2193 psia, represented by section E of the graph.

Figure 3:
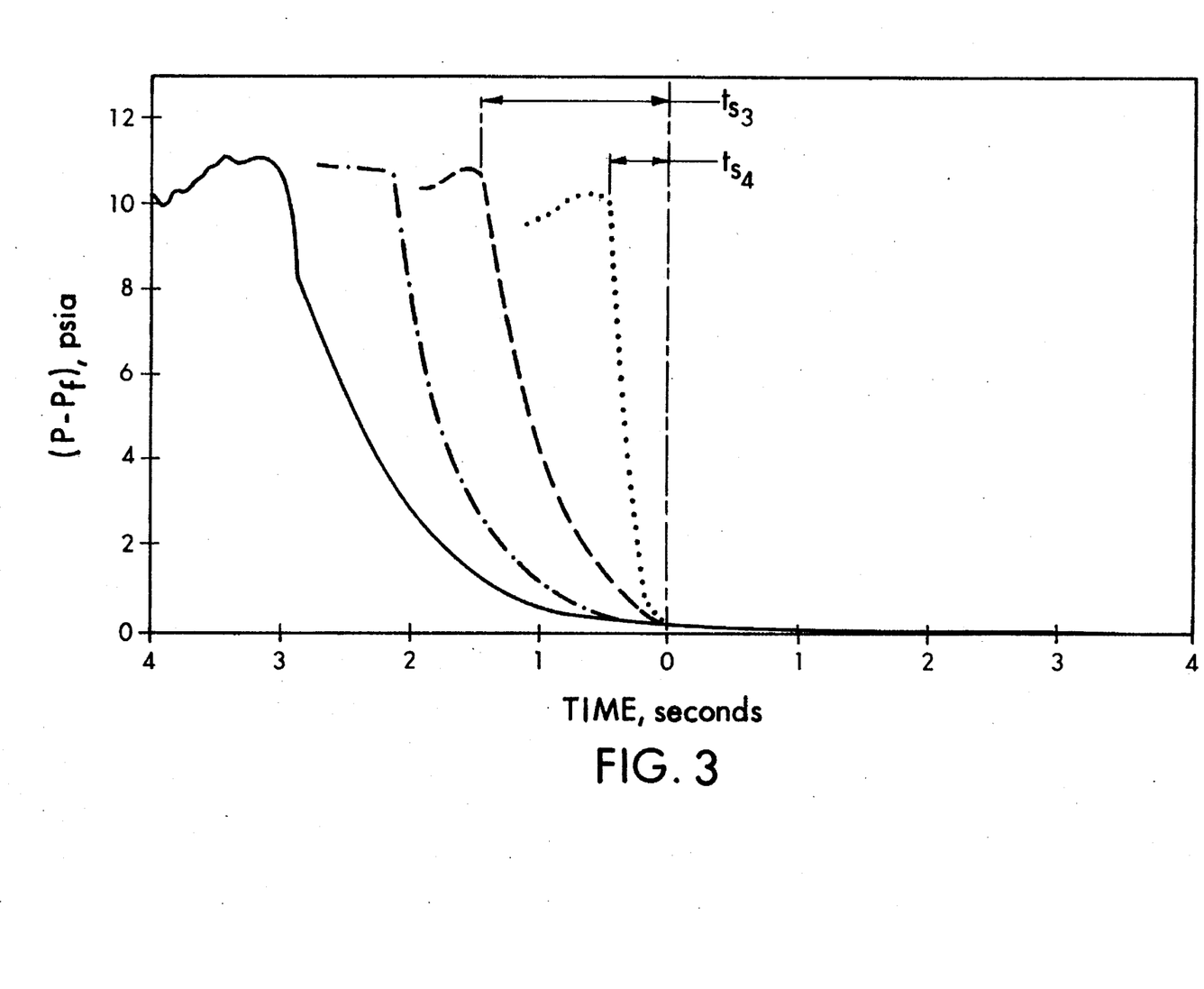
FIG. 3 is a graph of maximum cell pressure minus final cell pressure versus time for 4 bubbles with different final pressures.

In accordance with the present invention, one approach to determining the MMP is to look at the length of time $t_s$ required between bubble launch and stabilization at the final pressure. FIG. 3 shows data used to determine values of $t_s$ for bubbles of a gas rising in an oil in the apparatus shown in FIG. 1. The solid line represents measurements for which the final pressure ($p_f$) is 2244 psia. The mixed dashes and dots are for a final pressure of 2273 psia, the dashed line a final pressure of 2327 psia, and the dotted line a final pressure of 2369 psia. As the final pressure approaches the MMP, $t_s$ approaches a finite, very small, and nearly constant value.

Figure 4:
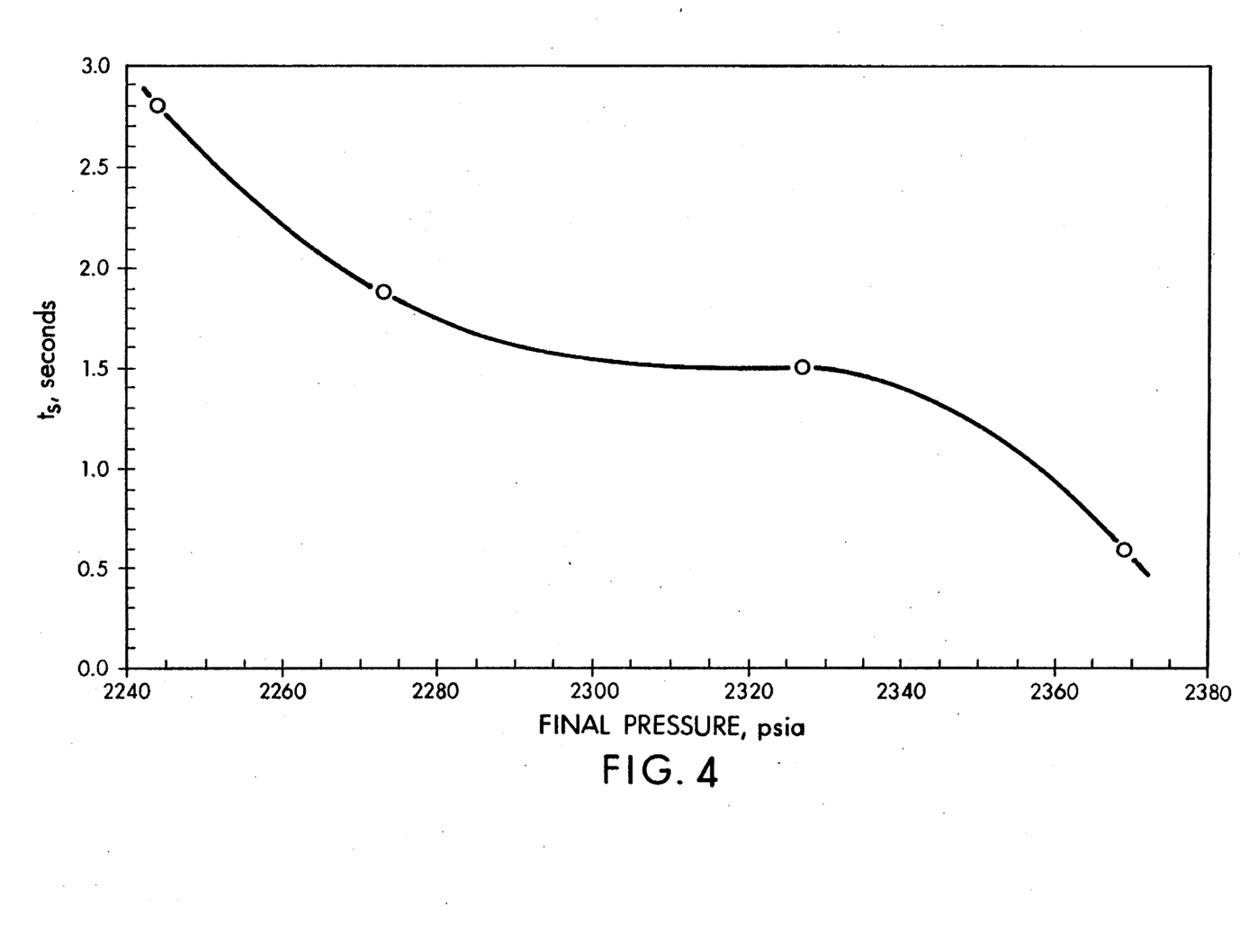
FIG. 4 is a graph of the time between bubble launch and the establishment of gas/liquid equilibrium versus final liquid pressure.

FIG. 4 is a graph showing $t_s$ as a function of final pressure, obtained at a given vessel pressure, for a different oil and a gas utilizing the apparatus of FIG. 1 and method of the present invention. The measurements shown in FIG. 4 are obtained at a constant temperature. When the final pressure is less than the MMP, $t_s$ bears an inverse relationship with final pressure. When the final pressure is at or slightly below the MMP, $t_s$ becomes constant and the slope of the curve becomes flat. When final pressure exceeds the MMP, $t_s$ and final pressure are again inversely related. The MMP determined by visual observations made with the same oil and gas in the same apparatus was 2332 psia.

Another approach to determining the MMP is to compare final pressure to initial pressure for a range of initial pressures at constant temperature. The relationship between the measured values of initial and final pressure can be approximated with a mathematical function, either graphically as illustrated in FIGS. 5 and 6 or by a numerical curve-fitting method as is known to one skilled in the art.

Figure 5:
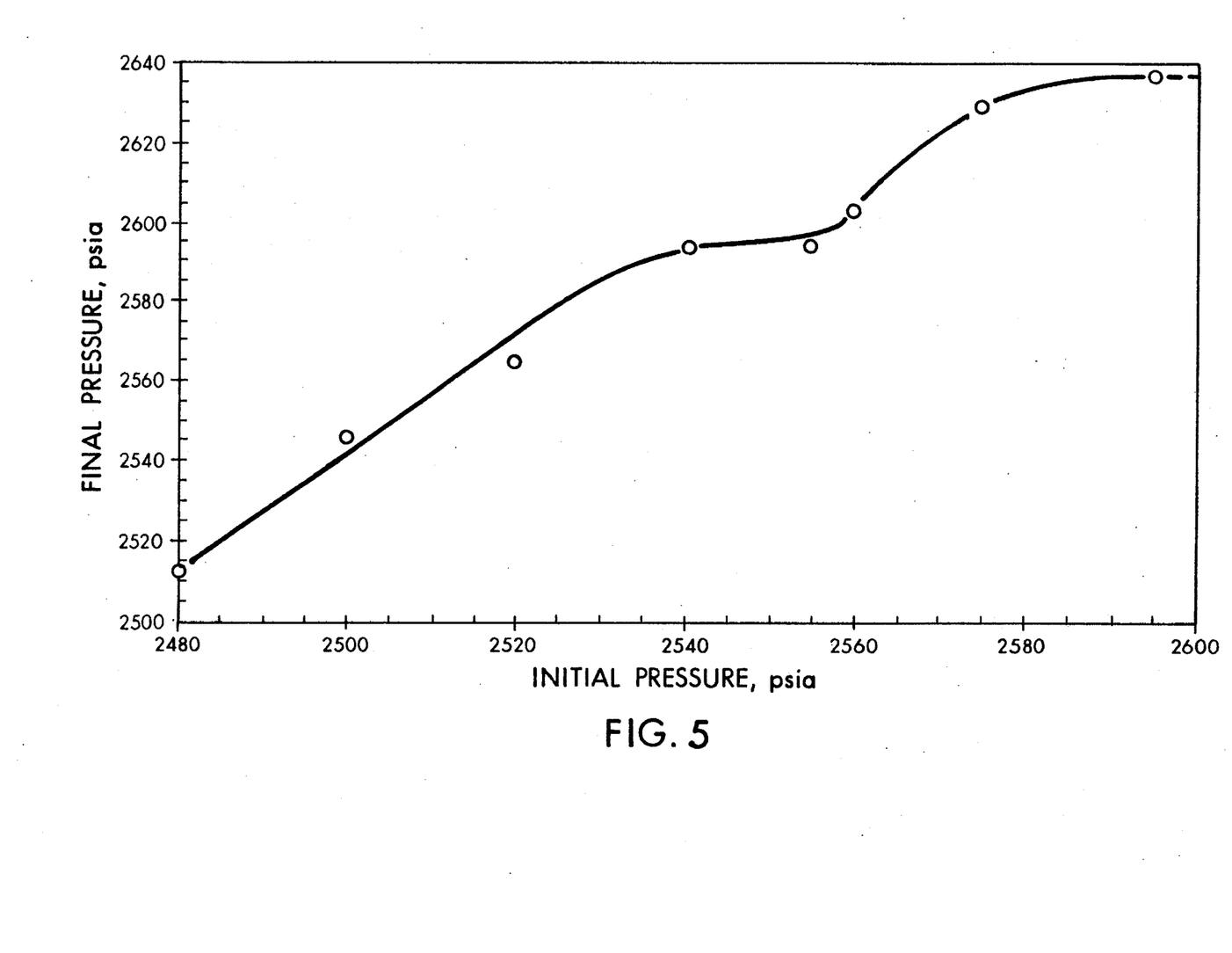
FIG. 5 is a graph of final pressure versus initial pressure for a vaporization process.

The data shown in FIG. 5 were obtained with a different oil for a vaporization process, in which liquid vaporizes at the upper boundary of the gas bubble and enters the bubble to achieve miscibility. When the final pressure is significantly less than the MMP, the final pressure increases with increases in the initial pressure. As the final pressure approaches the MMP, the first derivative of the function with respect to initial pressure or the slope of the line decreases to zero. When the final pressure exceeds the MMP, the derivative or slope again increases. Thus, the MMP can be determined by approximating the observed relationship with a mathematical function, taking the first derivative of the function, and finding the final pressure corresponding to a derivative value of zero. Alternatively, the MMP can be determined by graphing final pressure against initial pressure, as in FIG. 5, and reading the final pressure at the inflection point. The MMP determined from visual observations for the same oil and gas in the same apparatus, shown in FIG. 1, was 2594 psia.

Figure 6:
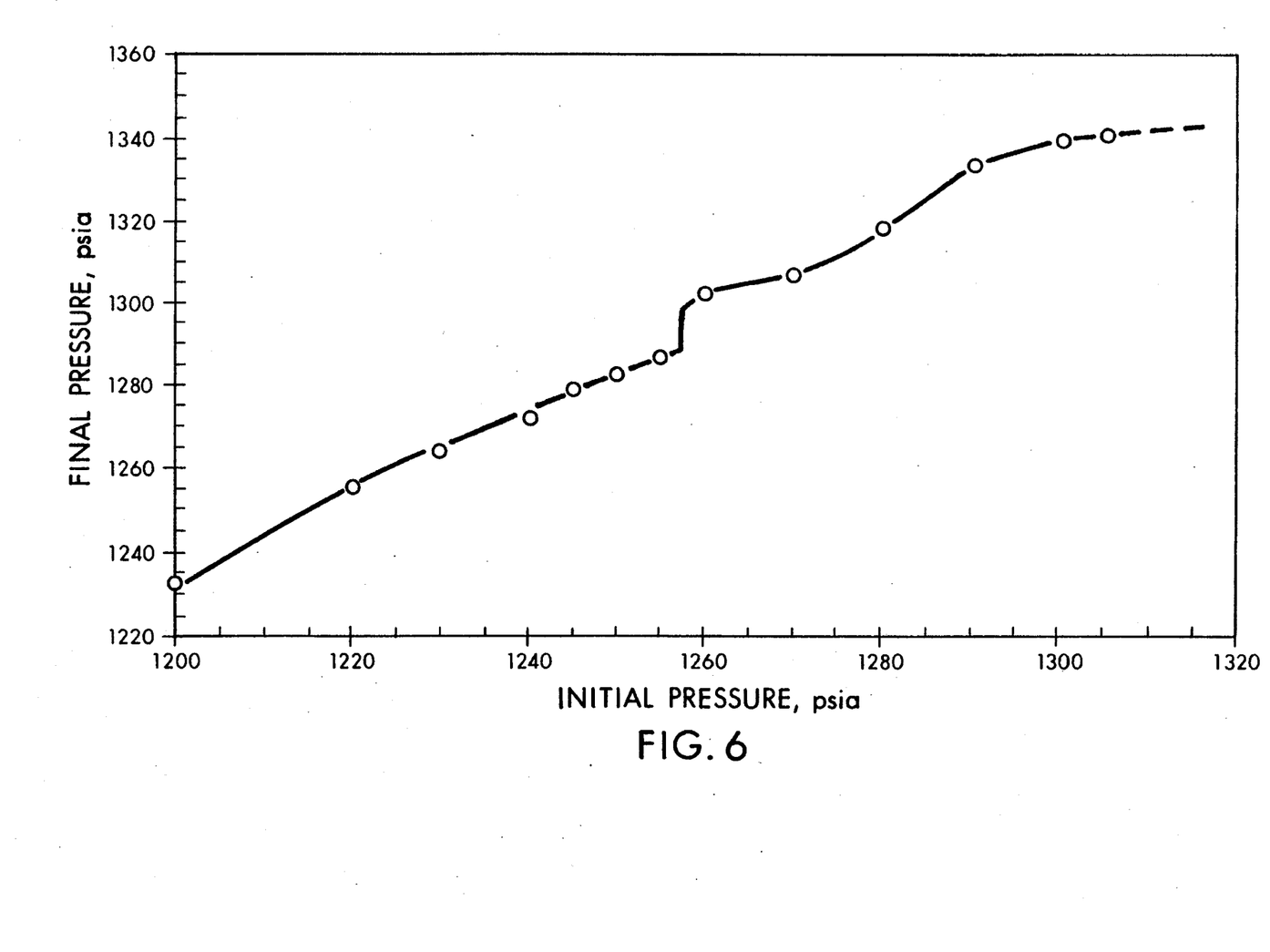
FIG. 6 is a graph of final pressure versus initial pressure for a condensation process.

FIG. 6 shows data obtained with another oil for a condensation process, in which miscibility results as the gas within the bubble condenses along the bubble boundary. In contrast to the vaporization process, there is a discontinuity of the slope of the line when the final pressure equals the MMP. Thus, the MMP can be determined graphically by reading the final pressure at which the discontinuity occurs, or by numerically finding the final pressure for which the derivative of the function with respect to initial pressure is undefined. The visually determined MMP was 1295 psia in the same apparatus, shown in FIG. 1.

Figure 7:
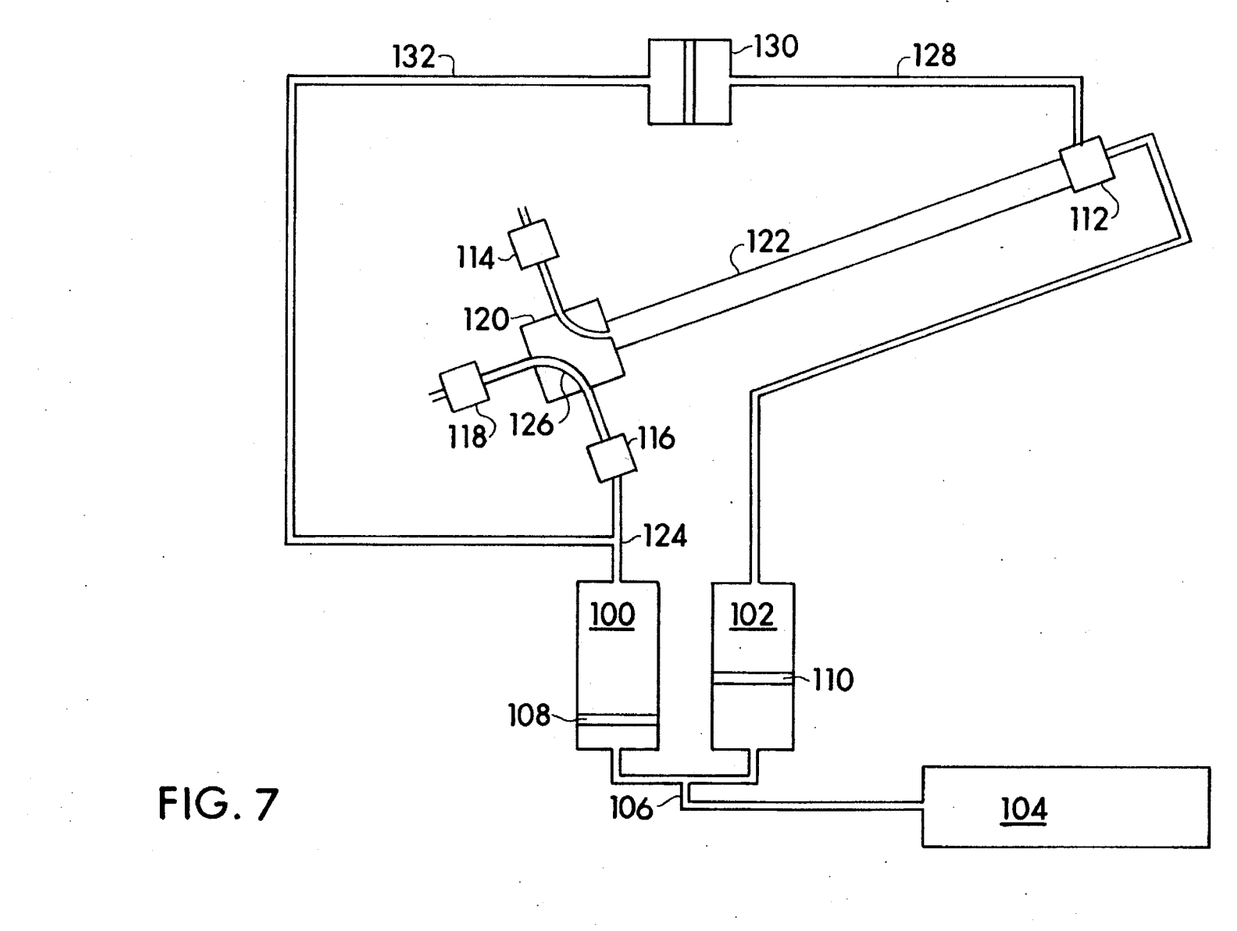
FIG. 7 is a schematic diagram of another embodiment of the apparatus of the present invention.

Another embodiment of an apparatus for determining MMPs is shown in FIG. 7. Gas reservoir 100 contains a gas, and liquid reservoir 102 contains a liquid. A means is provided for maintaining equal predetermined pressures in reservoirs 100 and 102. For example, a hydraulic fluid pump 104 and a hydraulic fluid line 106 can be used to move pistons 108 and 110 to maintain equal pressures in gas reservoir 100 and liquid reservoir 102. Valve 112 and liquid vent valve 114 control liquid flow into and out of tube 122. Valve 116 and gas vent valve 118 control gas flow into and, out of passage 126 in multiple valve 120. As shown, multiple valve 120 is a four-way valve. However, multiple valve 120 can be any means by which liquid communication between tube 122 and valve 114 and gas communication between passage 126 and tube 122 can each be established and cut off. Liquid pressure line 128 is in fluid communication with the interior of tube 122 and one side of pressure measuring device 130, and gas pressure line 132 is in fluid communication with gas line 124 and the other side of pressure measuring device 130.

When the apparatus shown in FIG. 7 is used to determine MMPs, valves 112, 114, 116, and 118 are initially closed, and multiple valve 120 is set to connect tube 122 with liquid vent valve 114 and gas, reservoir 100 with gas vent valve 118. Valves 116 and 118 are opened, allowing gas to flow through gas line 124 and passage 126 between gas reservoir 100 and gas vent valve 118, filling passage 126 between valves 11.6 and 118 with gas. Valves 116 and 118 are then closed. Valves 112 and 114 are opened, allowing liquid to flow through tube 122. Valves 114 and 112 are closed in succession, isolating the liquid in tube 122 at the same pressure as the gas in gas reservoir 100 and passage 126. Multiple valve 120 is then adjusted so that the gas in passage 126 is in fluid communication with the liquid in tube 122. The gas rises from passage 126 through tube 122 as a bubble. Tube 122 is tilted at an angle from horizontal to allow adequate contact time between the bubble and the liquid as the bubble rises through tube 122. The angle can be varied for different liquid/gas combinations. Pressure measuring device 130 measures the differential pressure between the liquid in tube 122 and the gas in gas line 124 and reservoir 100 as the bubble rises through tube 122. The gas reservoir pressure is kept constant during each experiment. The apparatus of FIG. 7 is charged with a single liquid and a gas.

As is apparent to those skilled in the art, the multiple contact miscibility process begins as soon as passage 126 is in fluid communication with tube 122. Due to the absence of the first liquid/second liquid interface, bubble launch occurs via a different mechanism than in the apparatus in FIG. 1. It is believed that liquid from the tube 122 seeps along the inner walls of passage 126 as material exchange occurs between the gas and the liquid. A bubble forms when liquid seeps to the bottom of passage 126 and completely encloses the gas remaining in the passage. The multiple contact miscibility process continues as the bubble then rises through the liquid in tube 122. Thus, the timing and rate of progression of the multiple contact miscibility process are different than with the apparatus of FIG. 1. The shapes of the curves in FIGS. 2–6 may differ from the shapes of comparable curves using data obtained with the apparatus of FIG. 7.

The process of the present invention has been described for the application of simulating enhanced oil recovery operations, in which the first liquid is a hydrocarbon. However, the apparatus and process could be utilized to determine the MMP of any gas/liquid combination at any temperature or pressure under which the apparatus is capable of operation. As is apparent to one skilled in the art, the temperature and pressure limitations of the apparatus are determined by the specific materials and methods used to construct the apparatus.

While the foregoing preferred embodiments of the inventions have been described and shown, it is understood that the alternatives and modifications, such as those suggested and others, may be made thereto and fall within the scope of the invention.

We claim:

1. A rising bubble apparatus for determining the minimum miscibility pressure of a comprising a gas and a liquid, the apparatus comprising;

a substantially enclosed pressure vessel;

a tube having an open end and a closed end and capable of being filled with a liquid held at an initial liquid pressure, the tube positioned within the pressure vessel with the end and end lower than the closed end;

means for forming gas bubbles at the bottom of the tube and launching bubbles into the liquid within the tube;

means for measuring liquid pressure changes occurring in said tube which pressure changes are relatively small compared with said initial liquid pressure, while bubbles of said gas form in said tube and move through said liquid and while material is exchanged between the liquid and the gas of individual bubbles.

2. The apparatus of claim 1 wherein said pressure measuring means comprises a pressure transducer in fluid communication with said liquid in said tube.

3. The apparatus of claim 2 wherein said pressure transducer comprises an absolute pressure transducer.

4. The apparatus of claim 2 wherein said pressure transducer is a differential pressure transducer, the transducer also in fluid communication with said gas.

5. The apparatus of claim 1 wherein said pressure changes measuring means communicates electrically with means for recording data.

6. The apparatus of claim 5 wherein said data recording means comprises a computer and software for receiving, storing, and retrieving said data.

7. The apparatus of claim 1 wherein said apparatus additionally comprises means for measuring time during bubble formation, launch, and ascent in said tube.

8. The apparatus of claim 1 wherein said tube is opaque.

9. The apparatus of claim 1 wherein said open end of said tube is capable of being opened or closed by a valve.

10. The apparatus of claim 9 wherein said valve is a multiple valve.

11. The apparatus of claim 10 wherein said means for forming and launching bubbles is a passage in a multiple valve.

12. The apparatus of claim 1 wherein said means for forming and launching bubbles is a hollow needle.

13. A method for determining the minimum miscibility pressure gas/liquid combination, the method comprising (a) filling a non-horizontal tube with said liquid and allowing said liquid to equilibrate at an predetermined temperature and initial pressure;

(b) forming and launching a single gas bubble into said liquid-filled tube;

(c) measuring pressure changes in said liquid which pressure changes are relatively small compared with said initial liquid pressure, while said bubble forms and rises through said liquid and the times at which pressure changes occur while material is exchanged between the liquid and gas of said bubbles;

(d) using said pressure changes to determine a bubble launch time when said bubble begins to rise through said liquid and a final pressure and final time when said bubble reaches equilibrium with said liquid;

(e) removing said liquid from said tube;

(f) repeating steps (a) through (e) at least one time, with said liquid at a different predetermined initial pressure for each repetition; and (g) determining a minimum final pressure for which the difference between the final time and the bubble launch time is approximately constant, said minimum final pressure being the minimum miscibility pressure of said gas in said liquid.

14. The method of claim 13 wherein steps (b) through (d) are repeated at least one time prior to removing said liquid from said tube.

15. The method of claim 13 wherein said liquid comprises hydrocarbons.

16. The method of claim 15 wherein said liquid comprises a crude

17. The method of claim 13 wherein said gas is selected from the group consisting of $CO_2$, $N_2$, $H_2S$, alkanes having up to 5 carbon atoms, and mixtures thereof.

18. A method for determining the minimum miscibility pressure of a gas/liquid, combination the method comprising:
   (a) filling a non-horizontal tube with said liquid and allowing said liquid to equilibrate at a predetermined temperature and initial pressure;
   (b) forming and launching a single gas bubble into said liquid in said tube;
   (c) measuring pressure changes in said liquid, which pressure changes relatively small compared with said initial liquid pressure as material is exchanged between the liquid and gas of said bubble, while said bubble forms and rises through said liquid;
   (d) determining the final pressure at which said bubble reaches equilibrium with said liquid;
   (e) emptying said liquid from said tube;
   (f) repeating steps (a) through (e) at least one time, with said liquid at a different predetermined initial pressure for each repetition:
   (g) deriving an empirical mathematical function relating the initial pressure to the final pressure: and
   (h) determining the final pressure at which the first derivative of said mathematical function with respect to initial pressure approaches a predetermined value, the final pressure at which said derivative approaches said value being the minimum miscibility pressure.

19. The method of claim 18 wherein a portion of said liquid and a portion of said gas in said bubble combine to form a second liquid having a composition intermediate between the compositions of said liquid and said gas, the second liquid vaporizes and enters said bubble, and said first derivative approaches a predetermined value of zero.

20. The method of claim 18 wherein a portion of said liquid and a portion of said gas in said bubble combine to form a second gas within said bubble having a composition intermediate between the compositions of said liquid and said gas, the second gas condenses and enters said liquid, and said first derivative approaches a predetermined value which is undefined.

21. The method of claim 18 wherein steps (b) through (d) are repeated at least one time prior to removing said liquid from said tube.

22. The method of claim 21 wherein said liquid comprises hydrocarbons.

23. The method of claim 21 wherein said liquid comprises a crude oil.

24. The method of claim 18 wherein said gas is selected from the group consisting of $CO_2$, $N_2$, $H_2S$, alkanes having up to 5 carbon atoms, and mixtures thereof.

* * * * *

UNITED STATES PATENT AND TRADEMARK OFFICE
CERTIFICATE OF CORRECTION

PATENT NO. : 5,505,074
DATED : April 9, 1996
INVENTOR(S) : I. Metin Mihcakan, Fred H. Poettmann, and Richard Christiansen It is certified that error appears in the above-indentified patent and that said Letters Patent is hereby corrected as shown below:

```
Col.3, line 48:    Delete "Combination" and insert --Pressure--.
Col.3, line 49:    Delete "system" and insert --combination--.
Col.3, line 61:    After "miscible" insert --,--.
Col.7, line 6 :    Delete "11.6" and insert --116--.
Col.7, line 58:    After "pressure of a" insert --combination--.
Col.7, line 64:    Delete "end and" and insert --open--.
```

Signed and Sealed this

Fifth Day of November, 1996

*Attest:*

BRUCE LEHMAN

*Attesting Officer*     Commissioner of Patents and Trademarks